United States Patent
Sklebitz et al.

[19]

[11] Patent Number: 6,154,520
[45] Date of Patent: Nov. 28, 2000

[54] X-RAY DIAGNOSTIC APPARATUS WITH AN X-RAY CONVERTER

[75] Inventors: Hartmut Sklebitz; Martin Hoheisel, both of Erlangen, Germany

[73] Assignee: Siemens Aktiengesellschaft, Munich, Germany

[21] Appl. No.: 09/259,460

[22] Filed: Mar. 1, 1999

[30] Foreign Application Priority Data

Feb. 27, 1998 [DE] Germany .................. 198 08 340

[51] Int. Cl.⁷ ................................................ H05G 1/64
[52] U.S. Cl. ..................... 378/98.8; 250/370.09; 250/370.11
[58] Field of Search ................ 378/98.8; 250/370.09, 250/370.11

[56] References Cited

U.S. PATENT DOCUMENTS 5,528,043  6/1996  Spivey et al. .
5,570,403  10/1996 Yamazaki et al. .

OTHER PUBLICATIONS

Patent Abstracts of Japan, 5 P 541, Application No. 60–41911.

"Das Röntgenfernsehen," Gebauer et al. pp. 26–33.

Primary Examiner—Craig E. Church
Attorney, Agent, or Firm—Schiff Hardin & Waite

[57] ABSTRACT

An X-ray diagnostic apparatus has an X-ray source that emits a diverging X-ray beam bundle that strikes a planar X-ray image converter at various angles, the converter having a substrate, image elements on the substrate arranged in a matrix with a semiconductor layer and a layer that absorbs X-ray beams. The X-ray-absorbing layer is fashioned thicker in the region at which a perpendicular ray of the X-ray beam bundle strikes the detector than in the region at which an oblique ray strikes, so that the reduction of the modulation transfer function in the region of an oblique beam incidence remains as small as possible.

14 Claims, 7 Drawing Sheets

X-RAY DIAGNOSTIC APPARATUS WITH AN X-RAY CONVERTER

BACKGROUND OF THE INVENTION

1. Field of the Invention

The present invention relates to an X-ray diagnostic apparatus of the type having an X-ray source that emits a diverging X-ray beam bundle that strikes a planar X-ray image converter at various angles, said converter having a substrate, with image elements on the substrate arranged in a matrix with a semiconductor layer and a layer that absorbs X-rays.

2. Description of the Prior Art

An X-ray diagnostic apparatus of the above general type is known, for example, from U.S. Pat. No. 5,528,043.

In many applications of such X-ray detectors, the X-rays do not strike the X-ray-sensitive surface of the X-ray detector perpendicularly, but rather obliquely. In methods employing projection geometry, for example radiography and transillumination, this leads to a worsening of the spatial resolution.

This effect is more pronounced 1) the closer the X-ray tube is to the X-ray detector,
2) the larger the lateral dimensions of the X-ray detector are,
3) the thicker the radiation-absorbing layer is, and
4) the finer the image point raster is in a digital image detector.

Mammography presents a particularly disadvantageous case. Here the distance from the X-ray focus to the X-ray detector or, respectively, film is typically only approximately 60 cm, in contrast to the standard distance of approximately 100 cm in radiography. Since the X-ray tube is arranged directly over the breast (chest) wall, the lateral extension from the striking point of the normal ray, calculated in the direction of the tip of the breast, amounts to the full edge length of the X-ray detector, while in radiography the normal ray strikes in the center of the detector, and thus only half the edge length must be taken into account. The image point raster is likewise very small, due to the required high spatial resolution. It typically has a value of <100 $\mu$m.

In order to achieve a high quantum absorption, the layer that absorbs the X-rays must be constructed as thick as possible, which results in the disturbing effect being further increased.

FIG. 1 shows the spatial resolution in the form of a simulated curve of the modulation transfer function (MTF curve). In FIG. 1, the contrast is plotted over the spatial frequency. The group of curves shows the course of the MTF in 4-cm steps from one locus directly underneath the X-ray tube (upper curve) up to a locus at a distance of up to 24 cm—the lowest curve corresponds to the MTF at a distance of 24 cm. A focus distance of 57 cm, a thickness of the absorbing layer of 200 $\mu$m and an image point raster of 85 $\mu$m are assumed. The MTF was approximated using the sinc function. It can be seen that the MTF clearly decreases toward the edge of the image. In the book "Das Röntgenfernsehen" by Gebauer et al., 2$^{nd}$ ed., Georg Thieme Verlag, Stuttgart, it is stated on pages 26ff that the threshold of recognizability is located at a spatial frequency at which the contrast has decreased to a value of 0.05 (see in particular page 28, right column, penultimate paragraph). This threshold value was plotted as a straight line in FIG. 1. It can thus be seen from FIG. 1 that, given perpendicular incidence, the resolution capacity of a spatial frequency of >10 lp/mm (line pairs per mm) decreases to as low as 4 at a distance of 24 cm.

This estimation of the MTF is, however, pessimistic, since at layer thicknesses that ensure a very high quantum efficiency (DQE), the absorption lengths of the X-ray radiation are smaller than the layer thickness. With selenium and an average quantum energy of 22 keV, for example, an average absorption length of 65 $\mu$m results.

From U.S. Pat. No. 5,570,403, a computed tomography apparatus is known that has various scintillator thicknesses.

In Japanese Application A 61-201 183, a scintillator is specified that is fashioned thinner in the middle detector region than in the outer detector region.

SUMMARY OF THE INVENTION

An object of the present invention is to provide an X-ray diagnostic apparatus of the type described above wherein the MTF remains approximately constant.

This object is achieved according to the invention in an X-ray diagnostic apparatus having an X-ray converter wherein the X-ray-absorbing layer is thicker in the region struck by an approximately perpendicular beam of the X-ray beam bundle than in the region at which an oblique ray strikes.

It has proven advantageous for the thickness of the layer that absorbs the X-rays to be fashioned in such a way that the reduction of the modulation transfer function (MTF) remains as low as possible in the region of an oblique beam incidence. It must thereby be taken into account that given a smaller layer thickness the quantum yield (DQE) decreases.

According to the invention, the thickness of the layer that absorbs the X-rays in the region of the approximately perpendicular ray incidence of the X-ray beam bundle can be constant.

Such an X-ray detector can be used for standard radiography if the thickness of that layer that absorbs the X-rays is constant in the middle of the X-ray image converter and is reduced at its lateral regions.

The X-ray detector can be used for mammographic exposures if the thickness of the X-ray-absorbing layer is constant in one lateral region of the X-ray image converter and decreases toward the other lateral region thereof. The side with the constant layer thickness faces the breast wall.

According to the invention, the thickness of the X-ray-absorbing layer can decrease outwardly from the region of the perpendicular ray incidence of the X-ray beam, i.e. from the central ray. This decrease takes place in a monotonic, non-linear fashion, e.g. according to a hyperbolic or cosine function, or in linear fashion.

It has proven advantageous for the X-ray-absorbing layer to be a semiconductor layer of amorphous selenium and for the image elements to contain switching elements. Alternatively, the X-ray-absorbing layer can be a scintillator and the image elements can be photodiodes. As a scintillator, cesium iodide or gadolinium oxisulfide can be used, and the photodiodes can be a semiconductor layer made of amorphous silicon.

DESCRIPTION OF THE PREFERRED EMBODIMENTS

Figure 2:
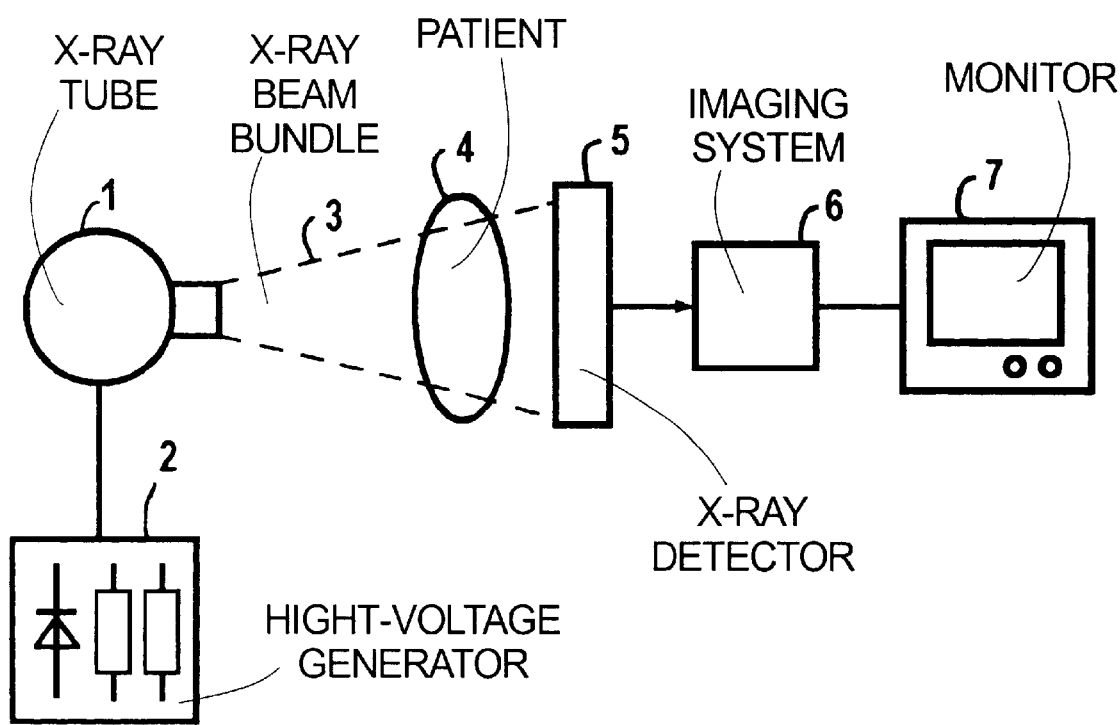
FIG. 2 shows a conventional X-ray diagnostic apparatus with an X-ray detector.

FIG. 2 shows a X-ray diagnostic apparatus with an X-ray tube 1, operated by a high-voltage generator 2. The X-ray tube 1 emits an X-ray beam bundle 3 that penetrates a patient 4 and strikes an X-ray detector 5, attenuated dependent on the transparency of the patient 4.

The X-ray detector 5, e.g. a solid-state image converter made of amorphous silicon (aSi:H), converts the X-ray image into electric signals, which are processed in a digital imaging system 6 connected thereto, the output of which is supplied to a monitor 7 for display of the X-ray image. The digital imaging system 6 can include, in a known manner, processing circuits, converters, difference-forming stages and image memories.

Figure 3:
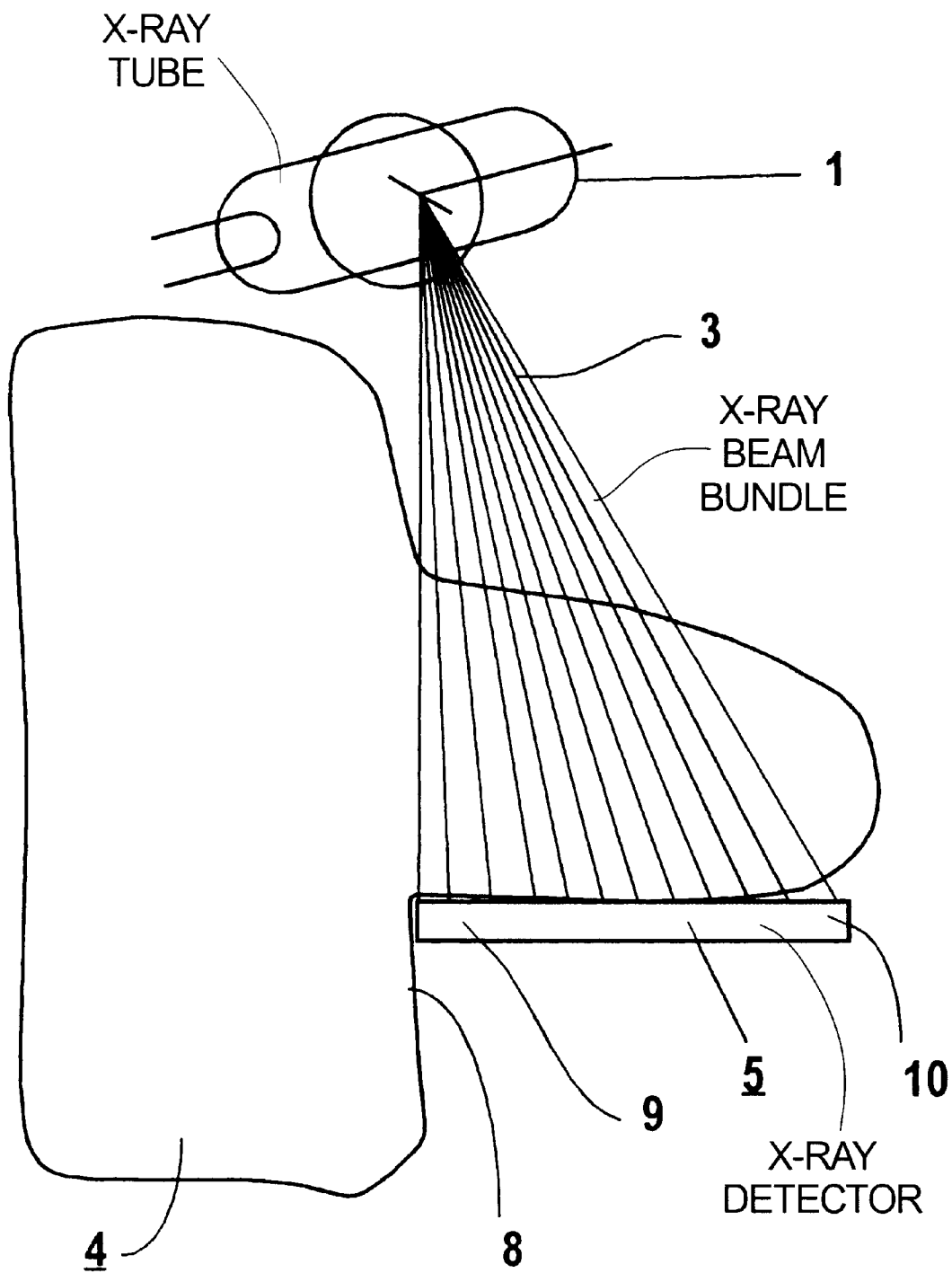
FIG. 3 shows a conventional X-ray apparatus for mammography with an X-ray detector, FIGS. 4 to 6 respectively show inventive X-ray detectors for various uses.

FIG. 3 schematically shows an X-ray apparatus for the production of mammographic exposures with the X-ray tube 1 arranged near the patient and opposite the X-ray detector 5 in such a way that anatomical details near the breast (chest) wall 8 of a patient 4 can be made clearly visible. This has the consequence that the X-rays are incident perpendicularly at a lateral region 9 of the X-ray detector 5, but is incident at the other lateral region of the X-ray detector 5 at an oblique angle.

Figure 4:
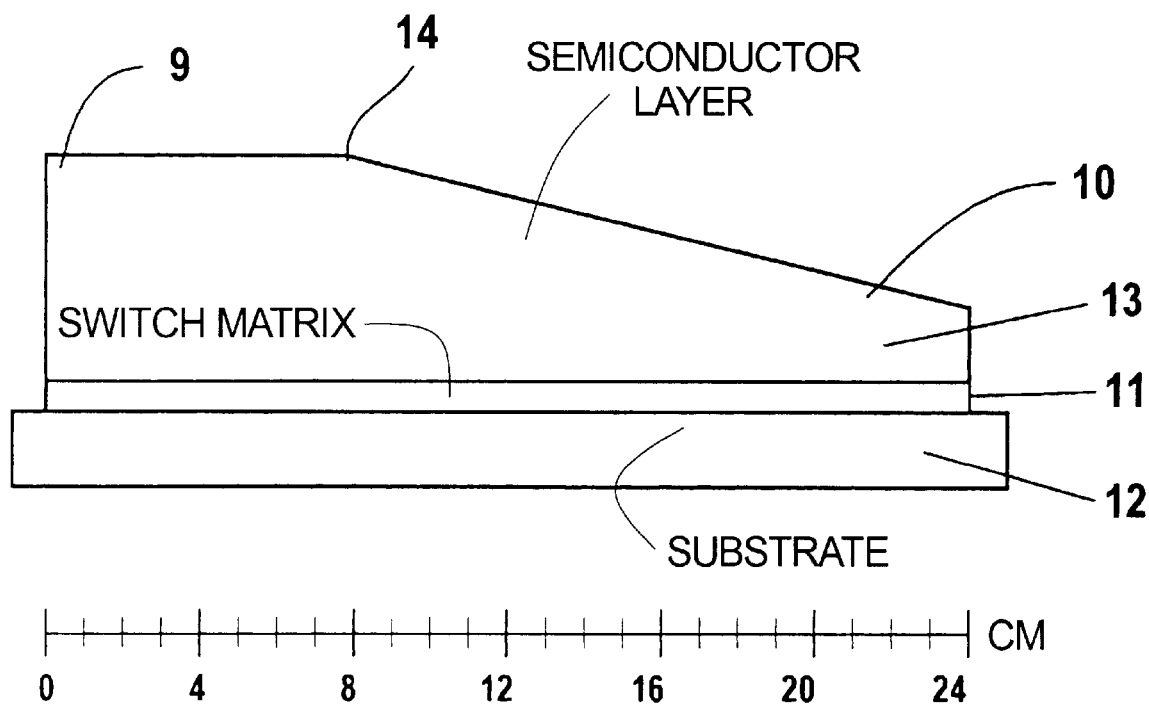

The inventive X-ray detector 5 shown in FIG. 4 includes, for example, a matrix 11 of thin-film switches that are preferably manufactured from amorphous silicon and are constructed on a glass substrate 12. Over this switch matrix 11, a semiconductor layer 13 made of amorphous selenium is applied as an X-ray-absorbing layer that absorbs the incoming X-ray quanta and converts them into charge carriers. The size of the active surface of this X-ray detector 5 can, for example, be 24×30 cm². The thickness of the semiconductor layer 13 is for example 200 μm in the lateral region 9 of the X-ray detector 5—which region faces the breast wall 8 during operation—and, after 8 cm, decreases toward the edge in a region 14, so that the semiconductor layer 13 is, for example, still 120 μm thick in the lateral region 10.

Figure 5:
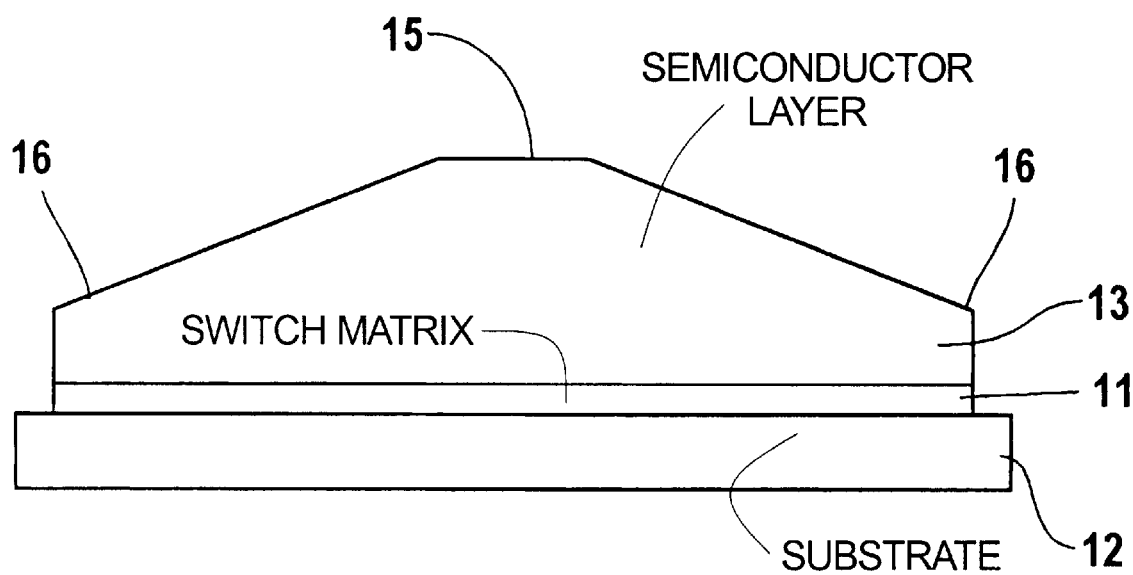

FIG. 5 shows a further inventive embodiment of an X-ray apparatus for radiographic exposures or for transillumination. The X-ray beam in this embodiment strikes perpendicularly at the center region 15 of the sensitive detector surface. This X-ray detector 5 also has a glass substrate 12 with a switch matrix 11. Amorphous selenium is again applied thereon as an X-ray-absorbing semiconductor layer 13.

If the switching matrix 11 additionally contains photodiodes, instead of the selenium layer a scintillator, such as e.g. cesium iodide or gadolinium oxisulfide, can be used as an X-ray-absorbing layer.

The thickness of the X-ray-absorbing layer 13 is selected as thick as possible in the center region 15 while still allowing the desired spatial resolution. This could, for example, be 500 μm. The layer thickness then decreases to e.g. 200 μm toward the lateral regions 16.

Figure 6:
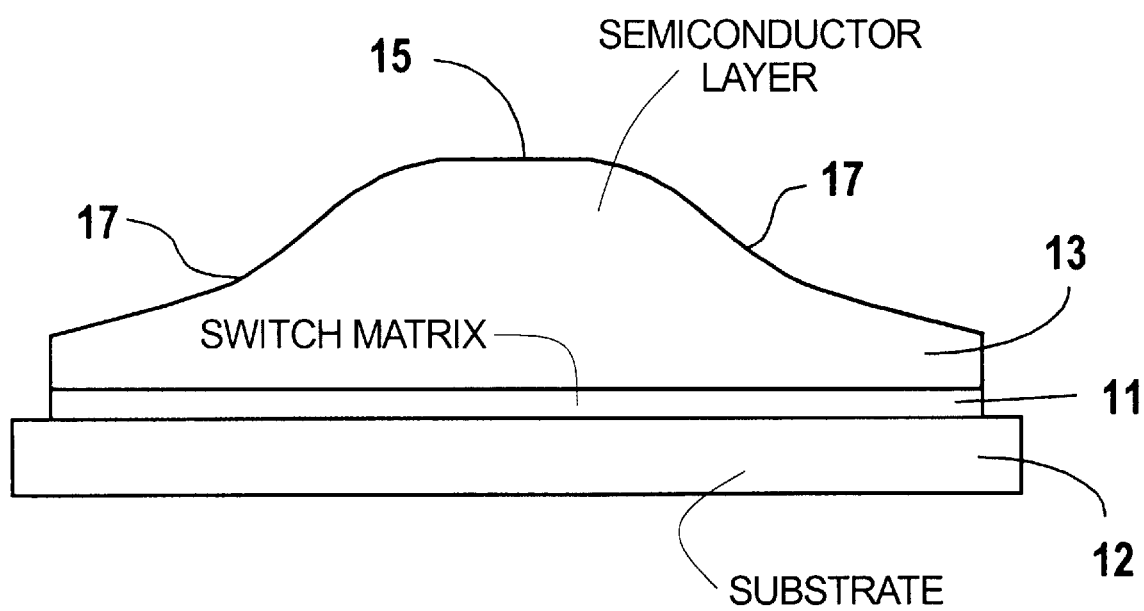

The decrease of the layer thickness need not take place in linear fashion; it can also alternatively follow a hyperbolic curve 17, as shown in FIG. 6, or can follow another function. Thus, the thickness of the X-ray-absorbing layer 13 can decrease from the region of the perpendicular ray incidence of the X-ray beam bundle 3 outwardly from a first layer thickness to a second layer thickness according to a cosine curve. This is dependent on which desired curve is technologically manufacturable.

Figure 1:
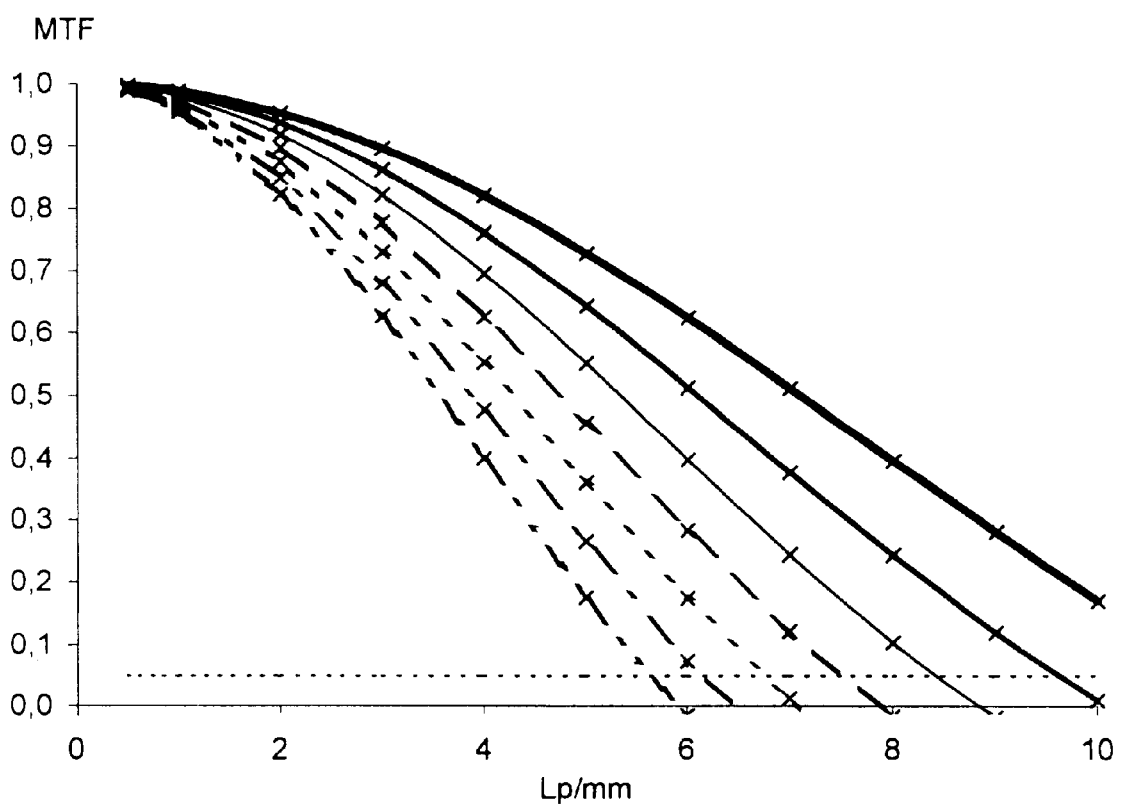
FIG. 1 shows a simulated spatial resolution in the form of MTF curves of an X-ray detector.
Figure 7:
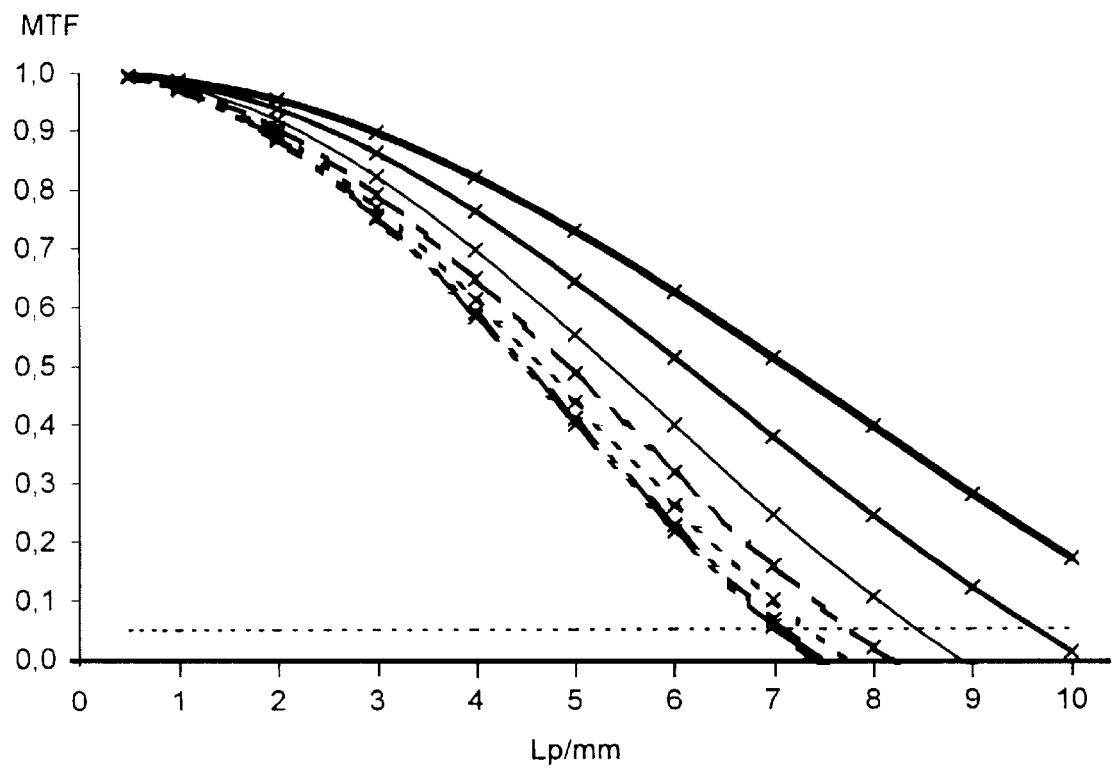
FIG. 7 shows a simulated spatial resolution in the form of MTF curves of an inventive X-ray detector.

By means of the inventive thickness reduction toward the edge of the X-ray-absorbing layer, the oblique incidence of the radiation is not so strongly noticeable, and the MTF also remains high toward the edge, as is shown in FIG. 7, in which the spatial resolution is shown as in FIG. 1, whereby between a distance of 8 and 24 cm the layer thickness was reduced in linear fashion from 200 μm to 120 μm. From FIG. 7 it can be seen that the resolution capacity of a spatial frequency of >10 lp/mm decreases to barely 7 lp/mm at a distance of 24 cm. The first three curves (0, 4 and 8 cm) are thereby unaltered, since the distance is not reduced until after 8 cm. The further curves are immediately adjacent to one another, so that the manner of operation of the reduction of the layer thickness can be seen clearly.

A disadvantage of such an arrangement could be that the X-ray absorption is smaller at the edge of the X-ray detector than in the center. This is compensated in part because the absorption path of the radiation is longer due to the oblique incidence.

The resulting decrease of the detector sensitivity, given reduced layer thickness, can be compensated without difficulty using a computer, in particular if an image-point-by-image-point gain correction is already provided anyway.

Heretofore, in the manufacture of X-ray detectors it was attempted to manufacture the X-ray absorbing layer as homogeneously as possible. This leads to a uniform brightness in the image. The MTF drop-off toward the edge was accepted.

Since newer digital X-ray detectors provide a compensation of the sensitivity for each image point, the drop-off in sensitivity is no longer an obstacle. The corrected signal is in any case homogeneously bright, and, with the inventively constructed layer thickness, also exhibits a practically homogenous spatial resolution.

According to the invention, the thickness profile of the layer should be planar at the location at which the normal of the incident radiation strikes the X-ray detector. Since the effect indicated above is small within a circle of a few cm around the center, the layer thickness can remain constant at that region. Further laterally outwardly, the layer thickness is then reduced in such a way that the MTF loss remains small due to the oblique radiation over the detector surface.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an X-ray diagnostic apparatus having an X-ray source which emits a diverging X-ray beam bundle, a planar X-ray image converter disposed in a path of said X-ray beam bundle which is struck by respective X-rays within said X-ray beam bundle at different angles, said converter comprising a substrate with a plurality of imaging elements disposed in a matrix on a semiconductor layer and an X-ray absorbing layer disposed on said substrate, the improvement comprising:

said X-ray absorbing layer having a thickness in a region of said X-ray absorbing layer struck by a perpendicular X-ray of said X-ray beam bundle greater than in a region struck by an oblique X-ray of said X-ray beam bundle.

2. The improvement of claim 1 wherein said X-ray absorbing layer has a modulation transmission function, and wherein said thickness of said X-ray absorbing layer at said region struck by said oblique X-ray has a modulation transfer function which is a minimum.

3. The improvement of claim 1 wherein said region struck by said perpendicular X-ray has a thickness which is substantially constant within said region struck by said perpendicular X-ray.

4. The improvement of claim 1 wherein said X-ray image converter has a center, and wherein said thickness of said X-ray absorbing layer is substantially constant at said center of said X-ray image converter and is reduced toward lateral regions of said X-ray image converter proceeding away from said center.

5. The improvement of claim 1 wherein said X-ray image converter has a center and a first lateral region proceeding away from a first side of said center and a second lateral region proceeding away from a second side of said center, and wherein said X-ray absorbing layer has a thickness which is constant in said first lateral region and which decreases from said center toward said second lateral region.

6. The improvement of claim 1 wherein said X-ray absorbing layer has a thickness which non-linearly decreases from said region struck by said perpendicular X-ray to said region struck by said oblique X-ray.

7. The improvement of claim 1 wherein said X-ray absorbing layer has a thickness which hyperbolically decreases from said region struck by said perpendicular X-ray to said region struck by said oblique X-ray.

8. The improvement of claim 1 wherein said X-ray absorbing layer has a thickness which decreases according to a cosine curve from said region struck by said perpendicular X-ray to said region struck by said oblique X-ray.

9. The improvement of claim 1 wherein said X-ray absorbing layer has a thickness which linearly decreases from said region struck by said perpendicular X-ray to said region struck by said oblique X-ray.

10. The improvement of claim 1 wherein said X-ray absorbing layer comprises a semiconductor layer of amorphous selenium, and wherein said imaging elements contain switching elements.

11. The improvement of claim 1 wherein said X-ray absorbing layer comprises a scintillator, and wherein said imaging elements comprise photodiodes.

12. The improvement of claim 11 wherein said scintillator consists of cesium iodide.

13. The improvement of claim 11 wherein said scintillator consists of gadolinium oxisulfide.

14. The improvement of claim 11 wherein said photodiodes each comprise a semiconductor layer of amorphous silicon.

* * * * *